(12) United States Patent
Funk et al.

(10) Patent No.: US 6,503,979 B1
(45) Date of Patent: Jan. 7, 2003

(54) METHOD FOR CROSS-LINKING HYDROGELS WITH BIS- AND POLY-2-OXAZOLIDINONES

(75) Inventors: Rüdiger Funk, Niedernhausen (DE); Volker Frenz, Mainz-Kostheim (DE); Ulrich Riegel, Frankfurt (DE); Matthias Weismantel, Jossgrund-Oberndorf (DE); Fritz Engelhardt, Chesapeake, VA (US); Thomas Daniel, Chesapeake, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/622,853

(22) PCT Filed: Feb. 24, 1998

(86) PCT No.: PCT/EP99/01188

§ 371 (c)(1),
(2), (4) Date: Aug. 28, 2000

(87) PCT Pub. No.: WO99/43720

PCT Pub. Date: Sep. 2, 1999

(30) Foreign Application Priority Data

Feb. 26, 1998 (DE) .......................................... 198 07 992

(51) Int. Cl.$^7$ ............................. C08F 8/30; A61C 15/00
(52) U.S. Cl. ...................... 524/556; 524/916; 525/107; 525/327.6; 525/329.9
(58) Field of Search .................. 525/327.6, 329.9, 525/375, 107; 524/556, 916

(56) References Cited

U.S. PATENT DOCUMENTS

| | | |
|---|---|---|
| 5,019,606 A | 5/1991 | Marten et al. |
| 5,331,059 A | 7/1994 | Engelhardt et al. |
| 5,385,983 A | 1/1995 | Graham |
| 5,840,822 A * | 11/1998 | Lee et al. ................. 528/44 |
| 6,140,388 A * | 10/2000 | Nass et al. .................. 523/139 |
| 2001/0025093 A1 * | 9/2001 | Ishikazi et al. ............. 526/210 |
| 2002/0061978 A1 * | 5/2002 | Hatsuda et al. .......... 525/330.1 |

FOREIGN PATENT DOCUMENTS

| | | |
|---|---|---|
| EP | 0 083 022 | 7/1983 |
| EP | 0 349 935 | 1/1990 |
| EP | 0 372 981 | 6/1990 |
| EP | 0 530 438 | 3/1993 |
| EP | 0 543 303 | 5/1993 |

* cited by examiner

*Primary Examiner*—D. R. Wilson
(74) *Attorney, Agent, or Firm*—Oblon, Spivak, McClelland, Maier & Neustadt, P.C.

(57) ABSTRACT

The invention contains a process for the surface post-crosslinking of water-absorbing polymers in which the polymers are treated with a surface postcrosslinking solution and during or after the treatment are postcrosslinked by means of an increase in temperature and are dried, wherein the crossinker comprises a bis-2-oxazolidinone or a poly-2-oxazolidinone comprising structural units of the formula

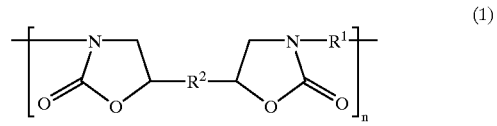

(1)

in which $R^1$ is branched or unbranched $C_1$–$C_{18}$-alkylene, branched or unbranched $C_2$–$C_{18}$-alkenylene, $C_5$–$C_{18}$-cycloalkylene, phenylene, naphthylene, anthracenylene, hydrocarbon-substituted phenylene, naphthylene or anthracenylene or another substituted or unsubstituted $C_6$–$C_{18}$-arylene radical, $R^2$ is branched or unbranched $C_1$–$C_{18}$-alkylene and n is an integer from 1 to 50 or a mixture of bis-2-oxazolidinones and poly-2-oxazolidinones dissolved in an inert solvent.

15 Claims, No Drawings

METHOD FOR CROSS-LINKING HYDROGELS WITH BIS- AND POLY-2-OXAZOLIDINONES

The present invention relates to a process for the gel or surface postcrosslinking of water-absorbing hydrogels by copolymerization of bis- and poly-2-oxazolidinones.

Hydrophilic highly swellable hydrogels are, in particular, polymers composed of (co)polymerized hydrophilic monomers, graft (co)polymers of one or more hydrophilic monomers on a suitable graft base, crosslinked cellulose ethers or starch ethers, crosslinked carboxymethylcellulose, partially crosslinked polyalkylene oxide, or natural products that are swellable in aqueous liquids, such as guar derivatives, for example. Hydrogels of this kind are used as products for absorbing aqueous solutions in the production of diapers, tampons, sanitary towels and other hygiene articles, and as water retainers in market gardening.

To improve service properties such as diaper rewet and AUL, for example, hydrophilic highly swellable hydrogels are generally subjected to surface or gel postcrosslinking. This postcrosslinking is known to the person skilled in the art and is preferably carried out in the aqueous gel phase or as surface postcrosslinking of the milled and sieved polymer particles.

Crosslinkers suitable for this purpose are compounds comprising at least two groups which are able to form covalent bonds with the carboxyl groups of the hydrophilic polymer. Examples of suitable crosslinkers are diglycidyl or polyglycidyl compounds, such as diglycidyl phosphonate, alkoxysilyl compounds, polyaziridines, polyamines or polyamidoamines, and these compounds can also be used in mixtures with one another (see for example EP-A-0 083 022, EP-A-0 543 303 and EP-A-0 530 438). Polyamidoamines which are suitable as crosslinkers are described in particular in EP-A-0 349 935.

A major disadvantage of these crosslinkers is their high reactivity. Although this is desirable in terms of chemical conversion it harbors a relatively high toxicological potential. The processing of such crosslinkers in the production plant requires special protective measures in order to meet the requirements of the relevant safety provisions and of occupational hygiene. In addition, the use of polymers modified in this way within hygiene articles appears questionable.

Polyfunctional alcohols are also known for use as crosslinkers. For example, EP-A-0 372 981, U.S. Pat. Nos. 4,666,983 and 5,385,983 teach the use of hydrophilic polyalcohols or the use of polyhydroxy surfactants. According to these documents the reaction is carried out at temperatures of 120–250° C. The process has the disadvantage that the esterification reaction which leads to crosslinking is relatively slow even at such temperatures.

The object was therefore, using compounds which are relatively slow to react yet which are reactive with carboxyl groups, to achieve gel or surface postcrosslinking which is as good if not better than that of the prior art, with as short as possible a reaction time and as low as possible a reaction temperature. Ideally, the prevailing reaction conditions should be the same as those obtained when highly reactive epoxides are used.

It has surprisingly now been found that this object can be achieved to outstanding effect with bis- and poly-2-oxazolidinones. In particular, the reactivity of these crosslinkers can be increased by adding organic or inorganic acidic catalysts. Suitable catalysts are the known inorganic mineral acids, their acidic salts with alkali metals or with ammonium, and their anhydrides. Suitable organic catalysts are the known carboxylic, sulfonic and amino acids.

The invention provides a process for the surface post-crosslinking of water-absorbing polymers in which the polymers are treated with a surface postcrosslinking solution and during or after the treatment are postcrosslinked by means of an increase in temperature and are dried, wherein the crosslinker comprises a bis-2-oxazolidinone or a poly-2-oxazolidinone comprising structural units of the formula

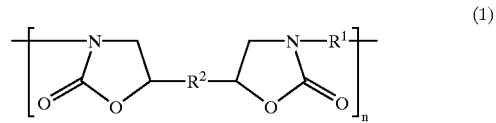

(1)

in which $R^1$ is branched or unbranched $C_1$–$C_{18}$-alkylene, branched or unbranched $C_2$–$C_{18}$-alkenylene, $C_5$–$C_8$-cycloalkylene, phenylene, naphthylene, anthracenylene, hydrocarbon-substituted phenylene, naphthylene or anthracenylene or another substituted or unsubstituted $C_6$–$C_{18}$-arylene radical, $R^2$ is branched or unbranched $C_1$–$C_{18}$-alkylene and n is an integer from 1 to 50 or a mixture of bis-2-oxazolidinones and poly-2-oxazolidinones dissolved in an inert solvent.

Where $R^1$ is an alkylene or alkenylene radical it is preferably one having a chain length of from 3 to 12, in particular from 5 to 10 carbon atoms. $R^2$ is preferably an alkylene radical having a chain length of from 3 to 12, in particular from 5 to 10, carbon atoms.

Terminal structural units of the formula 1 are endgroup-capped. The endgroup used can be any radical which can be introduced into the bis-2-oxazolidinones or poly-2-oxazolidinones and is chemically stable on these compounds. Examples of suitable radicals with which the structural units of the formula 1 can be endgroup-capped are hydrogen, branched or unbranched $C_1$–$C_{18}$-alkyl, branched or unbranched $C_2$–$C_{18}$-alkenyl, phenyl, naphthyl, anthracenyl, hydrocarbon-substituted phenyl, naphthyl or anthracenyl or another substituted or unsubstituted $C_6$–$C_{18}$-aryl radical.

The poly-2-oxazolidinones preferably comprise n bis-2-oxazolidinone units.

Preferably n is a number between 1 and 10, with particular preference between 3 and 6. The postcrosslinking temperature is preferably between 50 and 250° C., in particular 50–200° C. and especially 100–180° C.

To accelerate the surface postcrosslinking reaction, an acidic catalyst may be added to the reaction mixture. Catalysts which can be used in the process of the invention are all inorganic acids, their corresponding anhydrides, and/or organic acids and their corresponding anhydrides. Examples are boric, sulfuric, hydroiodic, phosphoric, tartaric, acetic and toluenesulfonic acid. Also suitable in particular are their polymeric forms, anhydrides, and the acid salts as occur, for example, in the case of the polybasic acids. Examples thereof are boron oxide, sulfur trioxide, diphosphorus pentoxide, and ammonium dihydrogen phosphate.

The process of the invention is preferably conducted by spraying a solution of the surface postcrosslinker onto the dry base polymer powder. Following spray application, the polymer powder is dried thermally, it being possible for the crosslinking reaction to take place either before or during drying. Preference is given to the spray application of a solution of the crosslinker in reaction mixers and spray mixers or mixing and drying systems, such as, for example, Lödige mixers, ®BEPEX mixers, ®NAUTA mixers, ®SHUGGI mixers or ®PROCESSALL apparatus. It is, moreover, also possible to employ fluidized-bed dryers. Drying can take place in the mixer itself, by heating the outer casing or by blowing in hot air. Likewise suitable is a downstream dryer, such as a shelf dryer, a rotary dryer or a heatable screw. Alternatively, azeotropic distillation, for example, can be utilized as a drying technique. The residence time at the preferred temperature in the reaction mixer or dryer is from 5 to 90 minutes, preferably less than 30 minutes and, with very particular preference, less than 10 minutes.

As an inert solvent, preference is given to water and to mixtures of water with simple or polyfunctional alcohols. It is, however, possible to employ all organic solvents of unlimited miscibility with water, examples being certain esters and ketones, which are not themselves reactive under the process conditions. Where an alcohol/water mixture is employed the alcohol content of this solution is 10–90% by weight, preferably 30–70% by weight and, in particular, 40–60% by weight. Any alcohol of unlimited miscibility with water can be employed, as can mixtures of two or more alcohols (e.g. methanol+glycerol+water). Particular preference is given to the use of the following alcohols in aqueous solution: methanol, ethanol, isopropanol, ethylene glycol and, with particular preference, 1,2-propanediol and also 1,3-propanediol. The surface postcrosslinking solution is employed in a proportion of 1–20% by weight based on the mass of polymer. Particular preference is given to a solution volume of 2.5–15% by weight based on polymer. The crosslinker itself is used in an amount of from 0.01–1.0% by weight based on the polymer employed.

The water-absorbing polymer is preferably a polymeric acrylic acid or a polyacrylate. This water-absorbing polymer can be prepared by a process known from the literature. Preference is given to polymers which include crosslinking comonomers (0.001–10 mol %) but very particular preference is given to polymers which have been obtained by means of free-radical addition polymerization using a polyfunctional ethylenically unsaturated free-radical crosslinker which in addition carries at least one free hydroxyl group (such as pentaerythritol triallyl ether or trimethylolpropane diallyl ether, for example).

The hydrophilic highly swellable hydrogels to be employed in the processes of the invention are, in particular, polymers of (co)polymerized hydrophilic monomers, graft (co)polymers of one or more hydrophilic monomers on a suitable graft base, crosslinked cellulose ethers or starch ethers, or natural products which are swellable in aqueous liquids, such as guar derivatives, for example. These hydrogels are known to the person skilled in the art and are described, for example, in U.S. Pat. No. 4,286,082, DE-C-27 06 135, U.S. Pat. No. 4,340,706, DE-C-37 13 601, DE-C-28 40 010, DE-A-43 44 548, DE-A-40 20 780, DE-A-40 15 085, DE-A-39 17 846, DE-A-38 07 289, DE-A-35 33 337, DE-A-35 03 458, DE-A-42 44 548, DE-A-42 19 607, DE-A-40 21 847, DE-A-38 31 261, DE-A-35 11 086. DE-A-31 18 172, DE-A-30 28 043, DE-A-44 18 881, EP-A-0 801 483, EP-A-0 455 985, EP-A-0 467 073, EP-A-0 312 952, EP-A-0 205 874, EP-A-0 499 774, DE-A-26 12 846, DE-A-40 20 780 EP-A-0 205 674, U.S. Pat. No. 5,145,906, EP-A-0 530 438, EP-A-0 670 073, U.S. Pat. Nos. 4,057,521, 4,062,817, 4,525,527, 4,295,987, 5,011,892, 4,076,663 or 4,931,497. The content of the abovementioned patent documents is expressly incorporated into the present disclosure by reference.

Examples of hydrophilic monomers suitable for preparing these hydrophilic highly swellable hydrogels are polymerizable acids, such as acrylic acid, methacrylic acid, vinylsulfonic acid, vinylphosphonic acid, maleic acid including its anhydride, fumaric acid, itaconic acid, 2-acrylamido-2-methylpropanesulfonic acid, 2-acrylamido-2-methylpropanephosphonic acid, and also their salts in each case, for example sodium, potassium or ammonium salts, their amides, hydroxyalkyl esters, and amino- or ammonium-functional esters and amides. Also suitable, furthermore, are water-soluble N-vinyl amides or else diallyldimethylammonium chloride. Preferred hydrophilic monomers are compounds of the formula 2

in which
R$^3$ is hydrogen, methyl or ethyl,
R$^4$ is —COOR$^6$, a sulfonyl group, a phosphonyl group, a (C$_1$–C$_4$)-alkanol-esterified phosphonyl group, or a group of the formula 3

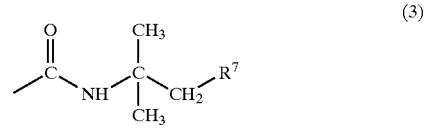

R$^5$ is hydrogen, methyl, ethyl or a carboxyl group,
R$^6$ is hydrogen, amino-(C$_1$–C$_4$)-alkyl or hydroxy-(C$_1$–C$_4$)-alkyl, an alkali metal ion or ammonium ion, and
R$^7$ is a sulfonyl group, a phosphonyl group or a carboxyl group, or alkali metal or ammonium salts of these groups.

Examples of (C$_1$–C$_4$)-alkanols are methanol, ethanol, n-propanol and n-butanol. Particularly preferred hydrophilic monomers are acrylic acid and methacrylic acid and also their alkali metal or ammonium salts, for example sodium, potassium and ammonium acrylate.

Suitable graft bases for hydrophilic hydrogels obtainable by graft copolymerization of olefinically unsaturated acids or their alkali metal or ammonium salts may be natural or synthetic in origin. Examples are starches cellulose and cellulose derivatives, and also other polysaccharides and oligosaccharides, polyalkylene oxides, especially polyethylene oxides and polypropylene oxides, and hydrophilic polyesters.

Suitable polyalkylene oxides have, for example, the formula

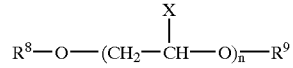

in which
R$^8$ and R$^9$ independently of one another are hydrogen, alkyl, alkenyl or acyl,
X is hydrogen or methyl, and
n is an integer from 1 to 10,000.
R$^8$ and R$^9$ are preferably hydrogen, (C$_1$–C$_4$)-alkyl, (C$_2$–C$_6$)-alkenyl or phenyl. Particularly preferred hydrogels are polyacrylates, polymethacrylates, and the graft copolymers described in U.S. Pat. Nos. 4,931,497, 5,011,892 and 5,041,496.

The hydrophilic highly swellable hydrogels are preferably in crosslinked form; that is, they include compounds having at least two double bonds which have been incorporated by copolymerization into the polymer network. Particularly suitable crosslinkers are methylenebisacrylamide and methylenemethacrylamide, esters of unsaturated mono- or polycarboxylic acids with polyols, such as diacrylate or triacrylate, examples being the diacrylate and dimethacrylate of butanediol and of ethylene glycol, and trimethylolpropane triacrylate, and also allyl compounds such as allyl (meth)acrylate, triallyl cyanurate, diallyl maleate, polyallyl esters, tetraallyloxyethane, triallylamine, tetraallylethylenediamine, allyl esters of phosphoric acid, and vinylphosphonic acid derivatives as are described, for example, in EP-A-0 343 427. In the process of the invention, however, particular preference is given to hydrogels prepared using polyallyl ethers as crosslinkers and by acidic homopolymerization of acrylic acid. Suitable crosslinkers are pentaerythritol tri- and tetraallyl ether, polyethylene glycol diallyl ether, monoethylene glycol diallyl ether, glycerol di- and triallyl ether, polyallyl ethers based on sorbitol, and alkoxylated variants thereof.

The hydrophilic highly swellable hydrogels can be prepared by conventional polymerization processes. Preference is given to addition polymerization in aqueous solution by the process known as gel polymerization. In this process from 15 to 50% by weight strength aqueous solutions of one or more hydrophilic monomers, and, if desired, of a suitable graft base are polymerized in the presence of a free-radical initiator, preferably without mechanical mixing, utilizing the Trommsdorff-Norrish effect (Makromol. Chem. 1 (1947) 169).

The polymerization reaction can be conducted in the temperature range between 0° C. and 150° C., preferably between 10° C. and 100° C., either at atmospheric pressure or under an increased or reduced pressure. The polymerization may also be performed in an inert gas atmosphere, preferably under nitrogen.

The polymerization can be initiated using high-energy electromagnetic radiation or by the customary chemical polymerization initiators. Examples of the latter are organic peroxides, such as benzoyl peroxide, tert-butyl hydroperoxide, methyl ethyl ketone peroxide and cumene hydroperoxide, azo compounds, such as azodiisobutyronitrile, and inorganic peroxi compounds, such as $(NH_4)_2S_2O_8$, $K_2S_2O_8$ or $H_2O_2$. These can if desired be used in combination with reducing agents such as sodium hydrogen sulfite, iron(II) sulfate, or redox systems. Redox systems include a reducing component, which is generally an aliphatic or aromatic sulfinic acid, such as benzenesulfinic acid or toluenesulfinic acid or derivatives of these acids, such as Mannich adducts of sulfinic acid, aldehydes and amino compounds as are described in DE-C-13 01 566.

The qualities of the polymers can be improved further by continuing to heat the polymer gels for a number of hours within the temperature range from 50 to 130° C., preferably from 70 to 100° C.

The resultant gels are neutralized to the extent of 0–100 mol % based on monomer employed, preferably 25–100 mol % and, with particular preference, 50–85 mol %, it being possible to use the customary neutralizing agents, preferably alkali metal hydroxides or alkali metal oxides, and with particular preference sodium hydroxide, sodium carbonate or sodium hydrogen carbonate. Neutralization is usually effected by mixing in the neutralizing agent as an aqueous solution or else, preferably, as a solid. For this purpose the gel is mechanically comminuted, by means for example of a mincer, and the neutralizing agent is sprayed on, scattered over or poured on, and then carefully mixed in. To effect homogenization the resultant gel mass may be passed through the mincer a number of times more.

The neutralized gel mass is then dried with a belt or roll dryer until the residual moisture content is less than 10% by weight, preferably below 5% by weight. The dried hydrogel is then ground and sieved, the usual candidates for grinding apparatus being roll mills, pin mills or vibrator mills. The preferred particle size of the sieved hydrogel lies in the range 45–1000 μm, with particular preference 45–850 μm, and, with very particular preference, 200–850 μm.

In accordance with the invention, acrylate-containing polymers are crosslinked using bis- or poly-2-oxazolidinones. The novel crosslinker of the invention can be prepared by reacting isocyanates and diepoxides (bis-2-oxazolidinones) or diisocyanates and diepoxides (poly-2-oxazolidinones).

The general equation for the formation of bis-2-oxazolidinones is as follows:

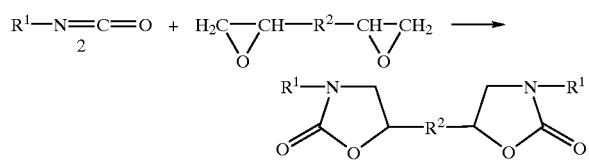

The formation of poly-2-oxazolidinones can be described by the general equation for the polyaddition:

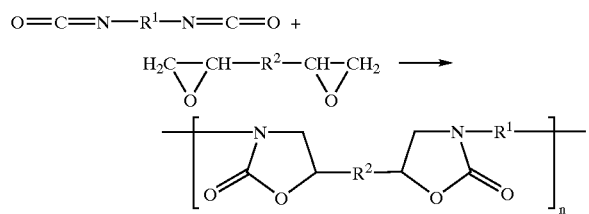

$R^1$ and $R^2$ are as defined above. In the preparation of poly-2-oxazolidinones it is possible to add a certain amount of monoisocyanates to the reaction mixture. These terminate the polyaddition when they are incorporated. The amount of monoisocyanates added must in this case be such as to lead to the desired chain length of the poly-2-oxazolidinones. The radical bearing the isocyanate group is then the end group. In the repeating unit of the polymer two oxazolidinone units have formed as a result of the polyaddition reaction, with n being an integer greater than 1. This polyaddition reaction takes place preferentially but not exclusively in polar aprotic solvents which react neither with the diisocyanate nor with the diepoxide at the prevailing temperature. Aliphatic diisocyanates produce with diepoxides pale products of low melting point which are soluble, for example, in dimethylformamide, whereas the reaction of aromatic diisocyanates generally leads to dark-colored and largely insoluble products of high melting point.

When aromatic diisocyanates are used the products are usually of poor solubility and high melting point, and it is therefore preferred to use aliphatic diisocyanates with aliphatic or aromatic diepoxides.

The invention also provides a product prepared by the process described above.

The invention additionally provides for the use of the products prepared by the process of the invention in hygiene articles, packaging materials and nonwovens.

In order to ascertain the quality of surface postcrosslinking, the dried hydrogel is then tested using the prior art test methods described below:

Methods

1) Centrifuge Retention Capacity (CRC)

This method measures the free swellability of the hydrogel in a teabag. Approximately 0.200 g of dry hydrogel are placed in a sealed teabag (format: 60 mm×60 mm, Dexter 1234T paper) and soaked for 30 minutes in 0.9% strength by weight sodium chloride solution. The teabag is then spun for 3 minutes in a commercially available spin dryer (Bauknecht WS 130, 1400 rpm, basket diameter 230 mm). The volume of liquid absorbed is determined by weighing the centrifuged teabag. The absorption capacity of the teabag itself is taken into account by determination of a blank value (teabag without hydrogel), which is deducted from the weighing result (teabag with swollen hydrogel).

Retention $CRC$ [g/g]=(weighing result teabag−blank value−initial weight of hydrogel)÷initial weight of hydrogel 2) Absorbency Under Load (0.3/0.5/0.7 psi)

For the absorbency under load, 0.900 g of dry hydrogel is distributed uniformly on the screen base of a measuring cell. The measuring cell consists of a Plexiglas cylinder (height= 50 mm, diameter=60 mm) whose base is formed by sticking on a screen of steel mesh (mesh size 36 microns, or 400 mesh). A cover plate is placed over the uniformly distributed hydrogel and loaded with an appropriate weight. The cell is then placed on a filter paper (S&S 589 black band, diameter=90 mm) lying on a porous glass filter plate, this filter plate itself lying in a Petri dish (height=30 mm, diameter=200 mm) which contains 0.9% strength by weight sodium chloride solution in an amount such that the liquid level at the beginning of the experiment is level with the top edge of the glass frit. The hydrogel is then left to absorb the salt solution for 60 minutes. Subsequently, the complete cell with the swollen gel is removed from the filter plate and the apparatus is back-weighed following removal of the weight.

The absorbency under load (AUL) is calculated as follows:

$AUL$[g/g]=$(W_b - W_a)/W_s$ where $W_b$ is the mass of the apparatus+gel after swelling, $W_a$ is the mass of the apparatus+initial weight of gel before swelling, and $W_s$ is the initial weight of dry hydrogel.

The apparatus consists of measuring cylinder and cover plate.

EXAMPLES

The examples according to the invention show the effect of the surface postcrosslinking on the superabsorbent polymers. As the person skilled in the art is aware, this postcrosslinking can be determined by measuring the centrifuge retention capacity (CRC) and the absorbency under load (AUL). With this surface crosslinking, the CRC typically falls by 5–10 g/g, whereas the AUL at 0.7 psi increases by approximately 10 and the AUL at 0.3 psi by more than 20 g/g.

Example 1

Base Polymer

In a 40 l plastic bucket, 6.9 kg of pure acrylic acid are diluted with 23 kg of water. 45 g of pentaerythritol triallyl ether are added with stirring to this solution, and the sealed bucket is rendered inert by passing nitrogen through it. The polymerization is then initiated by adding about 400 mg of hydrogen peroxide and 200 mg of ascorbic acid. After the end of the reaction the gel is mechanically comminuted and sodium hydroxide solution is added in an amount sufficient to achieve a degree of neutralization of 75 mol % based on the acrylic acid employed. The neutralized gel is then dried on a roll dryer, ground with a pin mill and, finally, isolated by sieving. This is the base polymer used in the subsequent examples.

Examples 1a and 1b

The base polymer is sprayed in a Waring laboratory mixer with a crosslinker solution of the following composition: 5% methanol, 5% water, 0.20% bisoxazolidinone from Preparation Example 1—based on polymer employed. Subsequently, a portion of the moist product is treated at 170° C. for 60 minutes and the remainder at 170° C. for 90 minutes, in a convection drying cabinet. The dried product is isolated by sieving at 850 microns in order to remove the lumps. This example shows that when bisoxazolidinones are used there is no need for any diol component in order to achieve surface postcrosslinking.

Examples 2a and 2b

Base polymer prepared as in Example 1 is sprayed with crosslinker solution in a Waring laboratory mixer. In this case the solution has a composition such that the following metering is achieved based on base polymer employed: 0.20% by weight bisoxazolidinone from Preparation Example 2, 5% by weight propylene glycol, 5% by weight water. The moist polymer is then dried at 175° C. for 30 and 60 minutes respectively.

Examples 3a and 3b

Base polymer prepared as in Example 1 is sprayed with crosslinker solution in a Waring laboratory mixer. In this case the solution has a composition such that the following metering is achieved based on base polymer employed: 0.20% by weight poly-2-oxazolidinone from Preparation Example 3, 5% by weight propylene glycol, 5% by weight water and 0.2% by weight boric acid. The moist polymer is then dried at 175° C. for 60 and 90 minutes respectively.

Examples 4a and 4b

Base polymer prepared as in Example 1 is sprayed with crosslinker solution in a Waring laboratory mixer. In this case the solution has a composition such that the following metering is achieved based on base polymer employed: 0.20% by weight poly-2-oxazolidinone from Preparation Example 4, 5% by weight propylene glycol, 5% by weight water and 0.2% by weight ammonium dihydrogen phosphate. The moist polymer is then dried at 175° C. for 60 and 90 minutes respectively.

Examples 5a and 5b

Base polymer prepared as in Example 1 is sprayed with crosslinker solution in a Waring laboratory mixer. In this case the solution has a composition such that the following metering is achieved based on base polymer employed: 0.20% by weight poly-2-oxazolidinone from Preparation Example 5, 5% by weight propylene glycol, 5% by weight water and 0.2% by weight ammonium dihydrogen phosphate. The moist polymer is then dried at 175° C. for 60 and 90 minutes respectively.

Examples 6a and 6b

Base polymer prepared as in Example 1 is sprayed with crosslinker solution in a Waring laboratory mixer. In this case the solution has a composition such that the following metering is achieved based on base polymer employed: 0.20% by weight bisoxazolidinone from Preparation Example 2, 5% by weight methanol, 5% by weight water and 0.2% by weight ammonium dihydrogen phosphate. This example shows that when bisoxazolidinones are used there is no need for any diol component in order to achieve surface postcrosslinking. The moist polymer is then dried at 175° C. for 60 and 90 minutes respectively.

Examples 7a and 7b

Base polymer prepared as in Example 1 is sprayed with crosslinker solution in a Waring laboratory mixer. In this case the solution has a composition such that the following metering is achieved based on base polymer employed: 0.20% by weight poly-2-oxazolidinone from Preparation Example 5, 5% by weight methanol, 5% by weight water and 0.2% by weight ammonium dihydrogen phosphate. This example shows that when poly-2-oxazolidinones are used there is no need for any diol component in order to achieve surface postcrosslinking. The moist polymer is then dried at 175° C. for 60 and 90 minutes respectively.

Preparation of a bis-2-oxazolidinone, Preparation Example 1 Reaction product of resorcinol diglycidyl ether and phenyl isocyanate In a three-necked flask with stirrer, reflux condenser and gas inlet pipe 0.1 mol of resorcinol diglycidyl ether (ABCR) is admixed dropwise with 0.2 mol of phenyl isocyanate (Aldrich) under a nitrogen atmosphere and the mixture is heated to the boiling point of DMF (Aldrich). The reaction solution is subsequently stirred under reflux for 3 to 4 hours and then cooled. The product is precipitated with methanol and recrystallized from DMF/methanol.

A brownish yellow compound having a melting point of 202° C. is obtained in high yield. The IR spectrum shows the typical band for oxazolidinones at 1750 cm$^{-1}$. The results of elemental analysis are: C, 67.2%; H, 5.3%; N, 6.0%.

Preparation of a bis-2-oxazolidinone

Preparation Example 2

Reaction Product of Bisphenol A Bisglycidyl Ether and Phenyl Isocyanate

In a three-necked flask with stirrer, reflux condenser and gas inlet pipe 0.1 mol of bisphenol A bisglycidyl ether (Aldrich) is admixed dropwise with 0.2 mol of phenyl isocyanate under a nitrogen atmosphere and the mixture is heated to the boiling point of DMF. The reaction solution is subsequently stirred under reflux for 3 to 4 hours and then cooled. The product is precipitated with methanol and recrystallized from water/methanol (3:1). A brownish yellow compound having a melting point of 131° C. is obtained in high yield. The IR spectrum shows the typical band for oxazolidinones at 1760 cm$^{-1}$. The results of elemental analysis are: C, 72.2%; H, 5.4%; N, 5.0%.

Preparation of poly-2-oxazolidinone

Preparation Example 3

In a three-necked flask with stirrer, reflux condenser and gas inlet pipe, 0.1 mol of bisphenol A diglycidyl ether is admixed dropwise with 0.1 mol of hexamethylene diisocyanate under a nitrogen atmosphere and the mixture is heated to the boiling point of DMF. The reaction solution is subsequently stirred under reflux for 3 to 4 hours and then cooled. The product is precipitated with water, redissolved in DMF and precipitated with water. The product dissolves in methanol and methanol/water mixtures. It is a white solid having a melting range between 105 and 120° C. and a Staudinger index in distilled water, $\eta_{sp}/c$, of 0.024 l/g.

Preparation of poly-2-oxazolidinone

Preparation Example 4

In a three-necked flask with stirrer, reflux condenser and gas inlet pipe, 0.1 mol of butanediol diglycidyl ether=1,4-bis-(2,3-epoxypropoxy)butane is admixed dropwise with 0.1 mol of hexamethylene diisocyanate under a nitrogen atmosphere and the mixture is heated to the boiling point of DMF. The reaction solution is subsequently stirred under reflux for 3 to 4 hours and then cooled. The product is precipitated with methanol and recrystallized from water/methanol (3:1). This gives a pale yellow oily liquid which is miscible with methanol and methanol/water.

Preparation of poly-2-oxazolidinone

Preparation Example 5

In a three-necked flask with stirrer, reflux condenser and gas inlet pipe, 0.1 mol of hexanediol diglycidyl ether=1,4-bis-(2,3-epoxypropoxy)hexane (ABCR) is admixed dropwise with 0.1 mol of hexamethylene diisocyanate under a nitrogen atmosphere and the mixture is heated to the boiling point of DMF. The reaction solution is subsequently stirred under reflux for 3 to 4 hours and then cooled. The product is precipitated with methanol and recrystallized from water/methanol (3:1). This gives a pale yellow oily liquid which is miscible with methanol and methanol/water.

| inventive examples | crosslinked with product from Preparation Example | drying temperature | drying time | catalyst/ solvent | CRC [g/g] | AUL 0.3 psi [g/g] | AUL 0.7 psi [g/g] |
|---|---|---|---|---|---|---|---|
| Example 1- Base polymer | — | — | — | — | 42 | 10 | 9 |
| Example 1a | 1 | 170° C. | 60 min | no cat. MeOH/H$_2$O | 35 | 36 | 21 |
| Example 1b | 1 | 170° C. | 90 min | no cat. MeOH/H$_2$O | 32 | 34 | 27 |
| Example 2a | 2 | 175° C. | 30 min | no cat. PG/H$_2$O | 35 | 35 | 27 |

-continued

| inventive examples | crosslinked with product from Preparation Example | drying temperature | drying time | catalyst/ solvent | CRC [g/g] | AUL 0.3 psi [g/g] | AUL 0.7 psi [g/g] |
|---|---|---|---|---|---|---|---|
| Example 2b | 2 | 175° C. | 60 min | no cat. PG/H$_2$O | 34 | 33 | 25 |
| Example 3a | 3 | 175° C. | 60 min | 0.2% H$_3$BO$_3$ PG/H$_2$O | 32 | 35 | 25 |
| Example 3b | 3 | 175° C. | 90 min | 0.2% H$_3$BO$_3$ PG/H$_2$O | 33 | 36 | 26 |
| Example 4a | 4 | 175° C. | 60 min | NH$_4$H$_2$PO$_4$ PG/H$_2$O | 34 | 34 | 24 |
| Example 4b | 4 | 175° C. | 90 min | NH$_4$H$_2$PO$_4$ PG/H$_2$O | 32 | 35 | 25 |
| Example 5a | 5 | 175° C. | 60 min | NH$_4$H$_2$PO$_4$ PG/H$_2$O | 33 | 36 | 24 |
| Example 5b | 5 | 175° C. | 90 min | NH$_4$H$_2$PO$_4$ PG/H$_2$O | 32 | 34 | 25 |
| Example 6a | 2 | 175° C. | 60 min | NH$_4$H$_2$PO$_4$ MeOH/H$_2$O | 32 | 29 | 20 |
| Example 6b | 2 | 175° C. | 90 min | NH$_4$H$_2$PO$_4$ MeOH/H$_2$O | 30 | 30 | 20 |
| Example 7a | 5 | 175° C. | 60 min | NH$_4$H$_2$PO$_4$ MeOH/H$_2$O | 32 | 31 | 21 |
| Example 7b | 5 | 175° C. | 90 min | NH$_4$H$_2$PO$_4$ MeOH H$_2$O | 31 | 30 | 19 |

Drying temperature and drying time refer here to the heat treatment of the base polymer sprayed with surface postcrosslinking solution.

We claim:

1. A process for the surface post-crosslinking of a water-absorbing polymer in which the polymer is treated with a surface postcrosslinking solution comprising a crosslinker and during or after the treatment are postcrosslinked by means of an increase in temperature and are dried, wherein the crosslinker comprises a bis-2-oxazolidinone or a poly-2-oxazolidinone comprising structural units of the formula

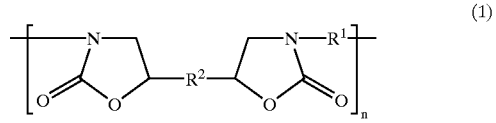

(1)

in which R$^1$ is branched or unbranched C$_1$–C$_{18}$-alkylene, branched or unbranched C$_2$–C$_{18}$-alkylene, phenylene, naphthylene, anthracenylene, hydrocarbon-substituted phenylene, naphtlylene or anthracenylene or another substituted or unsubstituted C$_6$–C$_{16}$-arylene radical, R$^2$ is branched or unbranched C$_1$–C$_{16}$-alkylene and n is an integer from 1 to 50 or a mixture of bis-2-oxazolidinones and polyoxazolidinones dissolved in an inert solvent,
wherein the bis-2-oxazolidinone or poly-2-oxazolidinone crosslinker is endgroup-capped by a radical, wherein said radical is selected from the group consisting of hydrogen, branched C$_1$–C$_{18}$-alkyl, unbranched C$_1$–C$_{18}$-alkyl, branched C$_2$–C$_{18}$-alkenyl, unbranched C$_2$–C$_{18}$-alkenyl, substituted C$_6$–C$_{18}$ aryl, or unsubstituted C$_6$–C$_{18}$ aryl.

2. The process as claimed in claim 1, wherein the water-absorbing polymer is a polymeric acrylic acid or a polyacrylate.

3. The process as claimed in claim 1, further comprising a catalyst for crosslinking, wherein the catalyst used for crosslinking is selected from the group consisting of an inorganic acid, an inorganic anhydride, a polymeric inorganic acid, an inorganic acid salt, an organic acid, an organic acid anhydride, and an organic acid salt.

4. The process as claimed in claim 3, wherein the catalyst is boric acid, sulfuric acid, phosphoric acid, or a polymer, anhydride or salt thereof, or hydriodic acid or salt thereof.

5. The process as claimed in claim 1, wherein the inert solvent is water, a mixture of water with an organic solvent of unlimited miscibility with water, or a mixture of water with a simple or polyfunctional alcohol.

6. The process as claimed in claim 5, wherein the simple or polyfunctional alcohol in said mixture of water with said simple or polyfunctional alcohol is 10–90% by weight.

7. The process as claimed in claim 5, wherein the simple or polyfunctional alcohol is methanol, ethanol, isopropanol, ethylene glycol, 1,2-propanediol or 1,3-propanediol.

8. The process as claimed in claim 1, wherein the surface postcrosslinking solution is employed in a proportion of 1–20% by weight, based on the mass of the polymer.

9. A liquid-absorbing polymer prepared by the process as claimed in claim 1.

10. The process as claimed in claim 1, wherein the water-absorbing polymer is a polymeric acrylic acid or a polyacrylate obtained by means of free-radical addition polymerization using a polyfunctional ethylenically unsaturated free-radical crosslinker which may in addition carry one or more free hydroxyl groups.

11. The process as claim in claim 1, wherein the surface postcrosslinking solution is employed in a proportion of 2.5–15% by weight, based on the mass of the polymer.

12. The process as claimed in claim 5, wherein the simple or polyfunctional alcohol in said mixture of water with said simple or polyfunctional alcohol is 30–70% by weight.

13. The process as claimed in claim 5, wherein the simple or polyfunctional alcohol in said mixture of water with said simple or polyfunctional alcohol is 40–60% by weight.

14. A hygiene article, packaging material or nonwoven comprising a water-absorbing hydrogel, wherein said water-absorbing hydrogel comprises a polymer produced by the process as claimed in claim 1.

15. The process as claimed in claim 3, wherein the catalyst is tartaric acid, acetic acid, toluenesulfonic acid, or an anhydride or salt thereof.

* * * * *

UNITED STATES PATENT AND TRADEMARK OFFICE
CERTIFICATE OF CORRECTION

PATENT NO.      : 6,503,979 B1
DATED           : January 7, 2003
INVENTOR(S)     : Funk et al.

It is certified that error appears in the above-identified patent and that said Letters Patent is hereby corrected as shown below:

<u>Title page,</u>
Item [22], PCT Filing Date should read: -- [22] PCT Filed: Feb. 24, 1999 --

Signed and Sealed this

Thirteenth Day of May, 2003

JAMES E. ROGAN
*Director of the United States Patent and Trademark Office*